(12) United States Patent
Bell et al.

(10) Patent No.: US 7,951,795 B2
(45) Date of Patent: May 31, 2011

(54) CONSTRAINED SPIROCYCLIC COMPOUNDS AS CGRP RECEPTOR ANTAGONISTS

(75) Inventors: Ian M. Bell, Harleysville, PA (US); Harold G. Selnick, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 107 days.

(21) Appl. No.: 12/517,674

(22) PCT Filed: Dec. 5, 2007

(86) PCT No.: PCT/US2007/024913
§ 371 (c)(1),
(2), (4) Date: Jun. 4, 2009

(87) PCT Pub. No.: WO2008/073251
PCT Pub. Date: Jun. 19, 2008

(65) Prior Publication Data
US 2010/0069359 A1 Mar. 18, 2010

Related U.S. Application Data

(60) Provisional application No. 60/873,854, filed on Dec. 8, 2006.

(51) Int. Cl.
C07D 521/00 (2006.01)
A61K 31/5517 (2006.01)
A61P 25/06 (2006.01)

(52) U.S. Cl. .................. 514/212.06; 540/521
(58) Field of Classification Search ........... 540/521; 514/212.06
See application file for complete search history.

(56) References Cited

U.S. PATENT DOCUMENTS

| | | |
|---|---|---|
| 7,189,722 B2 | 3/2007 | Bell et al. |
| 7,192,954 B2 | 3/2007 | Bell et al. |
| 7,202,251 B2 | 4/2007 | Bell et al. |
| 7,384,930 B2 | 6/2008 | Chaturvedula et al. |
| 7,384,931 B2 | 6/2008 | Chaturvedula et al. |
| 7,390,798 B2 | 6/2008 | Williams et al. |
| 2006/0094707 A1 | 5/2006 | Chaturvedula et al. |
| 2008/0004304 A1 | 1/2008 | Bell et al. |
| 2008/0096878 A1 | 4/2008 | Bell et al. |
| 2008/0214511 A1 | 9/2008 | Bell et al. |
| 2009/0054408 A1 | 2/2009 | Bell et al. |

FOREIGN PATENT DOCUMENTS

| | | |
|---|---|---|
| WO | WO03104236 | 12/2003 |
| WO | WO2004087649 | 10/2004 |
| WO | WO2006031676 | 3/2006 |
| WO | WO2006052378 | 5/2006 |
| WO | WO2008020902 | 2/2008 |
| WO | WO2008112159 | 9/2008 |
| WO | WO2008127584 | 10/2008 |
| WO | WO2008130512 | 6/2009 |

OTHER PUBLICATIONS

International Search Report and Written Opinion for PCT/US07/24913, dated Apr. 3, 2008.
Conner et al., The Second Intracellular Loop of the Calcitonin Gene-related Peptide Receptor Provides Molecular Determinants for Signal Transduction and Cell Surface Expression. J. Biol. Chem. Jan. 2006, 281(3):1644-1651.

*Primary Examiner* — Bruck Kifle
(74) *Attorney, Agent, or Firm* — Gerard M. Devlin; Raynard Yuro

(57) ABSTRACT

Compounds of formula I:

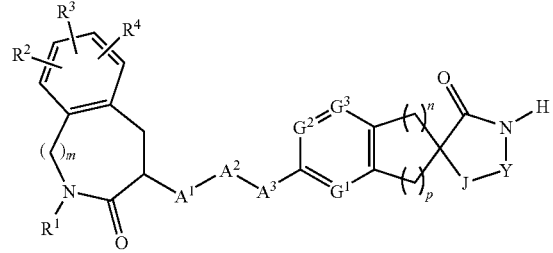

(wherein variables $A^1, A^2, A^3, G^1, G^2, G^3, J, m, n, p, R^1, R^2, R^3, R^4$ and Y are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

12 Claims, No Drawings

CONSTRAINED SPIROCYCLIC COMPOUNDS AS CGRP RECEPTOR ANTAGONISTS

CROSS-REFERENCE TO RELATED APPLICATIONS

This application claims priority under 35 U.S.C. §119(e) of U.S. provisional application Ser. No. 60/873,854, filed Dec. 8, 2006.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., hit. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, repetitive motion pain, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4 (4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

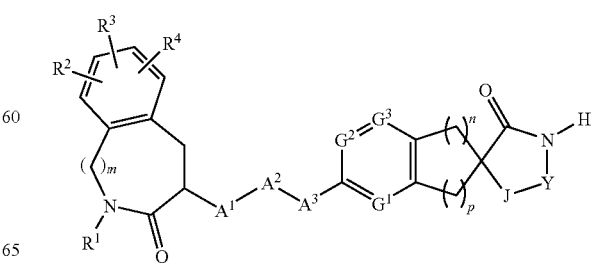

(wherein variables $A^1$, $A^2$, $A^3$, $G^1$, $G^2$, $G^3$, J, m, n, p, $R^1$, $R^2$, $R^3$, $R^4$ and Y are as described herein) which are antagonists of CGRP receptors and which are useful in the treatment or prevention of diseases in which the CGRP receptor is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

I wherein:
$R^1$ is selected from $C_{1-6}$alkyl, $C_{2-6}$alkenyl, $C_{3-7}$cycloalkyl, $C_{5-7}$cycloalkenyl, $C_{1-6}(C_{3-7}$cycloalkyl)alkyl, $C_{1-6}$haloalkyl, $C_{1-6}(C_{1-6}$alkoxy)alkyl, $C_{1-6}(Ar^1)$alkyl, $C_{1-6}(NR^7R^8)$alkyl, N—$(R^{16})$-pyrrolidinyl and N—$(R^{16})$-piperidinyl;
$R^2$ is hydrogen, halo, hydroxy, $C_{1-6}$alkyl, $C_{2-6}$alkenyl, benzyloxy, or $NR^7R^8$;
$R^3$ is hydrogen, hydroxy, halo, $C_{1-6}$alkyl, or $C_{2-6}$alkenyl, provided that if $R^2$ and $R^3$ are on adjacent carbon atoms they may together form —C(H)=N—N($R^9$), —thereby forming a fused ring;
$R^4$ is hydrogen, halo, $C_{1-6}$alkyl, or $C_{2-6}$alkenyl;
$R^7$ is hydrogen or $C_{1-6}$ alkyl;
$R^8$ is hydrogen or $C_{1-6}$alkyl;
or $NR^7R^8$ join to form a ring selected from the group consisting of pyrrolidinyl, piperidinyl, N—$(R^{16})$-piperazinyl, morpholinyl, and thiomorpholinyl;
$R^{16}$ is hydrogen, $C_{1-6}$alkyl, $C_{1-6}$alkylcarbonyl, or $C_{1-6}$alkoxycarbonyl;
$Ar^1$ is phenyl, naphthyl, pyridinyl, or imidazolyl, where $Ar^1$ is substituted with 0-2 substituents selected from the group consisting of halo, $C_{1-6}$alkyl, $C_{1-6}$haloalkyl,
$A^1$, $A^2$ and $A^3$ are each independently selected from:
  (1) a bond,
  (2) —$CR^{13}R^{14}$—,
  (3) —C(=O)—,
  (4) —O—,
  (5) —N($R^9$)—, or
  (6) —C(=N—CN)—,
    wherein one or two of $A^1$, $A^2$ and $A^3$ are optionally absent;
$G^1$, $G^2$ and $G^3$ are each independently selected from:
  (1) —C($R^5$)=,
  (2) —N=, and
  (3) —($N^+$—$O^-$)=;
J is independently selected from:
  (1) =C($R^{6a}$)—,
  (2) —$CR^{13}R^{14}$—,
  (3) —C(=O)—, and
  (4) —N($R^{15}$)—;

Y is independently selected from:
  (1) =C($R^{6b}$)—,
  (2) —$CR^{13}R^{14}$—,
  (3) —C(=O)—,
  (4) —$SO_2$—,
  (5) =N—, and
  (6) —N($R^{6b}$)—;
$R^5$ is independently selected from:
  (1) hydrogen,
  (2) $C_{1-6}$alkyl,
  (3) —O—$C_{1-6}$alkyl,
  (4) —$OCF_3$,
  (5) trifluoromethyl,
  (6) halo,
  (7) hydroxy, and
  (8) —CN;
$R^{6a}$ and $R^{6b}$ are each independently selected from:
  (1) hydrogen;
  (2) —$C_{1-4}$alkyl, which is unsubstituted or substituted with 1-5 substituents each independently selected from:
    (a) halo,
    (b) —O—$C_{1-6}$alkyl,
    (c) —$C_{3-6}$cycloalkyl,
    (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl,
      which phenyl or heterocycle is unsubstituted or substituted with 1-3 substituents each independently selected from:
        (i) —$C_{1-6}$ alkyl,
        (ii) —O—$C_{1-6}$alkyl,
        (iii) halo,
        (iv) hydroxy,
        (v) trifluoromethyl, and
        (vi) —$OCF_3$,
  (3) phenyl or heterocycle, wherein said heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl and morpholinyl, which phenyl or heterocycle is unsubstituted or substituted with 1-3 substituents where each independently selected from:
    (a) —$C_{1-4}$alkyl, which is unsubstituted or substituted with 1-5 fluoro,
    (b) halo,
    (c) hydroxy,
    (d) —O—$C_{1-4}$ alkyl, which is unsubstituted or substituted with 1-5 fluoro,
    (e) —$C_{3-6}$cycloalkyl, and
    (f) phenyl,
  (4) halo,
  (5) hydroxy,
  (6) —O—$C_{1-6}$alkyl, which is unsubstituted or substituted with 1-5 halo,
  (7) —CN,
  (8) —$CO_2R^9$,
  (9) —$NR^{10}R^{11}$, and
  (10) —$CONR^{10a}R^{11a}$;
or where $R^{6a}$ and $R^{6b}$ join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) hydroxy,
    (iii) —O—$C_{1-6}$alkyl,
    (iv) —$C_{3-6}$cycloalkyl,
    (v) phenyl or heterocycle, wherein said heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$C_{1-6}$alkyl,
      (II) —O—$C_{1-6}$alkyl,
      (III) halo,
      (IV) hydroxy,
      (V) trifluoromethyl, and
      (VI) —$OCF_3$,
    (vi) —$CO_2R^9$,
    (vii) —$NR^{10}R^{11}$,
    (viii) —$SO_2R^{12}$,
    (ix) —$CONR^{10a}R^{11a}$, and
    (x) —$(NR^{10a})CO_2R^9$,
  (b) phenyl or heterocycle, wherein said heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
    (i) —$C_{1-6}$alkyl, which is unsubstituted or substituted with 1-6 fluoro,
    (ii) halo,
    (iii) hydroxy,
    (iv) —O—$C_{1-6}$alkyl, which is unsubstituted or substituted with 1-6 fluoro, and
    (v) —$C_{3-6}$cycloalkyl,
  (c) halo,
  (d) —$SO_2R^{12}$,
  (e) hydroxy,
  (f) —O—$C_{1-6}$alkyl, which is unsubstituted or substituted with 1-5 halo,
  (g) —CN,
  (h) —$COR^{12}$,
  (i) —$NR^{10}R^{11}$,
  (j) —$CONR^{10a}R^{11a}$,
  (k) —$CO_2R^9$,
  (l) —$(NR^{10a})CO_2R^9$,
  (m) —$O(CO)NR^{10a}R^{11a}$,
  (n) —$(NR^9)(CO)NR^{10a}R^{11a}$, and
  (o) oxo;
$R^9$ is independently selected from:
  (1) hydrogen,
  (2) —$C_{1-6}$alkyl, which is unsubstituted or substituted with 1-6 fluoro,
  (3) —$C_{3-6}$cycloalkyl,
  (4) benzyl, and
  (5) phenyl;
$R^{10}$ and $R^{11}$ are each independently selected from:
  (1) hydrogen,
  (2) $C_{1-6}$ alkyl, which is unsubstituted or substituted with 1-6 fluoro,
  (3) —$C_{5-6}$cycloalkyl,
  (4) benzyl,
  (5) phenyl,
  (6) —$COR^9$, and
  (7) —$SO_2R^{12}$;
$R^{10a}$ and $R^{11a}$ are each independently selected from:
  (1) hydrogen,
  (2) —$C_{1-6}$ alkyl, which is unsubstituted or substituted with 1-6 fluoro,
  (3) —$C_{5-6}$cycloalkyl,
  (4) benzyl, and
  (5) phenyl;
or $R^{10a}$ and $R^{11a}$ join to form a ring selected from azetidinyl, pyrrolidinyl, piperidinyl, piperazinyl and morpholinyl, which ring is unsubstituted or substituted with 1-5 substituents each independently selected from: —$C_{1-6}$alkyl, —O—$C_{1-6}$alkyl, halo, hydroxyl, phenyl and benzyl;
$R^{12}$ is independently selected from:
  (1) —$C_{1-6}$alkyl, which is unsubstituted or substituted with 1-6 fluoro,
  (2) —$C_{5-6}$cycloalkyl,
  (3) benzyl, and
  (4) phenyl;
$R^{13}$ and $R^{14}$ are each independently selected from:
  (1) hydrogen,
  (2) —$C_{1-6}$ alkyl, which is unsubstituted or substituted with 1-6 fluoro,
  (3) hydroxy, and
  (4) halo;
$R^{15}$ is selected from:
  (1) —$C_{1-6}$alkyl and —$C_{3-6}$cycloalkyl, which is unsubstituted or substituted with 1-7 substituents each independently selected from:
    (a) halo,
    (b) hydroxy,
    (c) —O—$C_{1-6}$alkyl,
    (d) —$C_{3-6}$cycloalkyl,
    (e) phenyl, which is unsubstituted or substituted with 1-5 substituents each independently selected from:
      (i) —$C_{1-6}$alkyl,
      (ii) —O—$C_{1-6}$alkyl,
      (iii) halo,
      (iv) hydroxy, and
      (v) trifluoromethyl,
    (f) —$CO_2R^9$,
    (g) —$NR^{10}R^{11}$,
    (h) —$CONR^{10}R^{11}$,
    (i) —$SO_2R^{12}$, and
    (j) trifluoromethyl, and
  (2) phenyl or heterocycle, wherein said heterocycle is selected from: pyridyl, pyrimidinyl, pyrazinyl, thienyl and morpholinyl, which phenyl or heterocycle is unsubstituted or substituted with 1-5 substituents each independently selected from:
    (a) —$C_{1-6}$ alkyl,
    (b) —O—$C_{1-6}$alkyl,
    (c) halo,
    (d) hydroxy, and
    (e) trifluoromethyl;
m is 0 or 1;
n is 1 or 2;
p is 1 or 2;
and pharmaceutically acceptable salts thereof and individual enantiomers and diastereomers thereof.

An embodiment of the present invention includes compounds of the formula Ia:

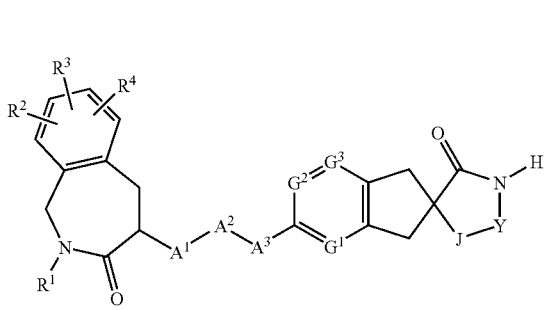

Ia wherein $A^1$, $A^2$, $A^3$, $G^1$, $G^2$, $G^3$, J, Y, $R^1$, $R^2$, $R^3$ and $R^4$ are defined herein;

and pharmaceutically acceptable salts thereof and individual enantiomers and diastereomers thereof.

Another embodiment of the present invention includes compounds of the formula Ib:

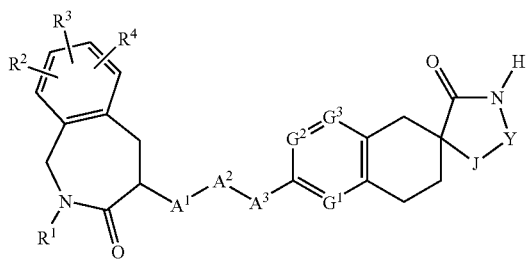

Ib wherein $A^1$, $A^2$, $A^3$, $G^1$, $G^2$, $G^3$, J, Y, $R^1$, $R^2$, $R^3$ and $R^4$ are defined herein;

and pharmaceutically acceptable salts thereof and individual enantiomers and diastereomers thereof.

Another embodiment of the present invention includes compounds of the formula Ic:

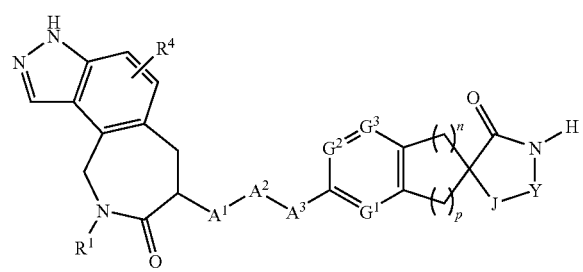

Ic wherein $A^1$, $A^2$, $A^3$, $G^1$, $G^2$, $G^3$, J, Y, $R^1$, $R^4$, n and p are defined herein;

and pharmaceutically acceptable salts thereof and individual enantiomers and diastereomers thereof.

Another embodiment of the present invention includes compounds of the formula Id:

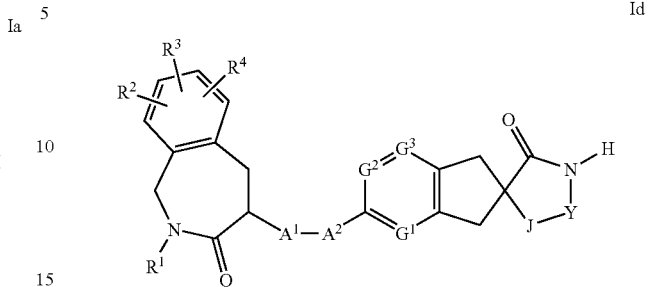

Id wherein $A^1$, $A^2$, $G^1$, $G^2$, $G^3$, J, Y, $R^1$, $R^2$, $R^3$ and $R^4$ are defined herein;

and pharmaceutically acceptable salts thereof and individual enantiomers and diastereomers thereof.

Another embodiment of the present invention includes compounds of the formula Ie:

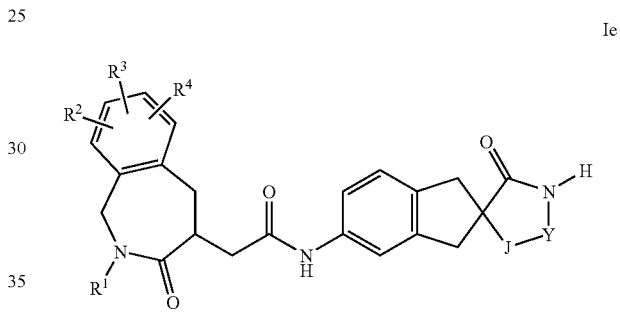

Ie wherein J, Y, $R^1$, $R^2$, $R^3$ and $R^4$ are defined herein;

and pharmaceutically acceptable salts thereof and individual enantiomers and diastereomers thereof.

Another embodiment of the present invention includes compounds of the formula If:

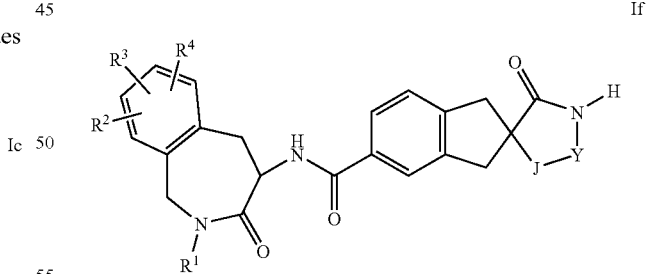

If wherein J, Y, $R^1$, $R^2$, $R^3$ and $R^4$ are defined herein;

and pharmaceutically acceptable salts thereof and individual enantiomers and diastereomers thereof.

In an embodiment of the present invention $A^1$ is a bond.
In an embodiment of the present invention $A^1$ is —CH$_2$—.
In an embodiment of the present invention $A^1$ is —O—.
In an embodiment of the present invention $A^1$ is —NH—.
In an embodiment of the present invention $A^2$ is a —C(=O)—.
In an embodiment of the present invention $A^2$ is —CH$_2$—.
In an embodiment of the present invention $A^2$ is —O—.

In an embodiment of the present invention $A^2$ is —NH—.
In an embodiment of the present invention $A^3$ is a —C(=O)—.
In an embodiment of the present invention $A^3$ is —CH$_2$—.
In an embodiment of the present invention $A^3$ is —O—.
In an embodiment of the present invention $A^3$ is —NH—.
In an embodiment of the present invention $G^1$ is —C(H)=.
In an embodiment of the present invention $G^1$ is —N=.
In an embodiment of the present invention $G^2$ is —C(H)=.
In an embodiment of the present invention $G^2$ is —N=.
In an embodiment of the present invention $G^3$ is —C(H)=.
In an embodiment of the present invention $G^3$ is —N=.
In an embodiment of the invention, one of $G^1$, $G^2$ and $G^3$ is —N=.
In an embodiment of the present invention J is selected from:
=C(R$^{6a}$)—; —N(Me)—; and —CH$_2$—; wherein R$^{6a}$ is defined herein.
In an embodiment of the present invention J is —CH$_2$—.
In an embodiment of the present invention J is =C(R$^{6a}$)—; wherein R$^{6a}$ is defined herein.
In an embodiment of the present invention J is —N(CH$_3$)—.
In an embodiment of the present invention Y is selected from:
=C(R$^{6b}$)—; —CH$_2$—; and —C(=O)—; wherein R$^{6b}$ is defined herein.
In an embodiment of the present invention Y is —CH$_2$—.
In an embodiment of the present invention Y is —C(=O)—.
In an embodiment of the present invention Y is =C(R$^{6b}$)—; wherein R$^{6b}$ is defined herein.
In an embodiment of the present invention $R^2$ and $R^3$ taken together are —C(H)=N—N(R$^9$)—.
In an embodiment of the present invention $R^4$ is independently selected from hydrogen, halo, and methyl.
In an embodiment of the present invention R$^{6a}$ and R$^{6b}$ are independently selected from:
(1) hydrogen;
(2) —C$_{1-4}$alkyl, which is unsubstituted or substituted with 1-3 substituents each independently selected from: halo, —O—C$_{1-6}$alkyl, —C$_{3-6}$cycloalkyl, and phenyl,
(3) phenyl or heterocycle, wherein heterocycle is selected from: pyridyl, pyrimidinyl, pyrazinyl, thiazolyl, oxazolyl, tetrahydrofuryl, piperidinyl, and morpholinyl, which phenyl or heterocycle is unsubstituted or substituted with 1-3 substituents each independently selected from: —C$_{1-4}$ alkyl which is unsubstituted or substituted with 1-3 fluoro, —O—C$_{1-4}$alkyl which is unsubstituted or substituted with 1-3 fluoro, halo and hydroxyl,
(4) halo,
(5) —NR$^{10}$R$^{11}$,
(6) hydroxy,
(7) —O—C$_{1-4}$alkyl which is unsubstituted or substituted with 1-3 halo.
In an embodiment of the present invention R$^{6a}$ and R$^{6b}$ are independently selected from:
(1) hydrogen;
(2) —C$_{1-4}$ alkyl which is unsubstituted or substituted with 1-3 fluoro, and
(3) phenyl or heterocycle, wherein heterocycle is selected from: pyridyl, pyrimidinyl, pyrazinyl, thiazolyl, oxazolyl, tetrahydrofuryl, piperidinyl and morpholinyl.
In an embodiment of the present invention R$^{6a}$ and R$^{6b}$ join to form a ring selected from phenyl, pyridyl, pyrimidinyl, pyrazinyl, pyridazinyl, thiazolyl, oxazolyl, imidazolyl and thienyl, which ring is unsubstituted or substituted with 1-3 substituents each independently selected from:
(a) —C$_{1-4}$ alkyl, which is unsubstituted or substituted with 1-3 substituents each independently selected from: halo, —O—C$_{1-6}$alkyl, —CO$_2$R$^9$, —NR$^{10}$R$^{11}$ and —CONR$^{10a}$R$^{11a}$,
(b) phenyl or heterocycle, wherein heterocycle is selected from: pyridyl, pyrimidinyl, pyrazinyl, pyrrolidinyl, azetidinyl, piperidinyl and morpholinyl, which phenyl or heterocycle is unsubstituted or substituted with 1-3 substituents each independently selected from: —C$_{1-4}$ alkyl, which is unsubstituted or substituted with 1-5 fluoro, —O—C$_{1-4}$ alkyl, which is unsubstituted or substituted with 1-3 fluoro, halo and hydroxyl,
(c) halo,
(d) hydroxy,
(e) —O—C$_{1-6}$ alkyl, which is unsubstituted or substituted with 1-5 halo,
(f) —CN,
(g) —NR$^{10}$R$^{11}$,
(h) —CONR$^{10a}$R$^{11a}$, and
(i) oxo.

In an embodiment of the present invention R$^{6a}$ and R$^{6b}$ join to form a ring selected from phenyl, pyridyl, and pyrimidinyl, which ring is unsubstituted or substituted with 1-3 substituents each independently selected from: —C$_{1-4}$alkyl which is unsubstituted or substituted with 1-3 fluoro, halo, hydroxy and —O—C$_{1-4}$ alkyl.

In an embodiment of the present invention R$^{6a}$ and R$^{6b}$ and the atom(s) to which they are attached are joined to form a ring selected from pyridyl and pyrimidinyl.

In an embodiment of the present invention m is 1.
In an embodiment of the present invention n is 1.
In an embodiment of the present invention p is 1.
In an embodiment of the present invention p is 2.

It is to be understood that where one or more of the above recited structures or substructures recite multiple substituents having the same designation each such variable may be the same or different from each similarly designated variable. For example, R$^{16}$ is recited multiple times in formula I, and each R$^{16}$ in formula I may independently be any of the substructures defined under R$^{16}$. The invention is not limited to structures and substructures wherein each R$^{16}$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^7$ and $R^8$ substituents are capable of forming a ring structure. This is also the case with respect to other potentially ring forming pairs, including but not limited to $R^{6a}$ and $R^{6b}$ and $R^{10a}$ and $R^{11a}$. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. Related terms such as "alkoxy", "haloalkyl" and "alkoxycarbonyl" also include such straight, branched and cyclic moieties.

"Alkenyl" means a straight, branched or cyclic group with at least one double bond.

A term such as $C_{1-6}(R)$alkyl means a straight or branched alkyl group of one to six carbons substituted with the substituent R. A term such as N—(R)-pyrrolidinyl indicates that the nitrogen is substituted with the substituent R.

"Haloalkyl" and "haloalkoxy" include all halogenated isomers from monohalo substituted alkyl to perhalo substituted alkyl. The same applies to other moieties described with "halo".

The term "heterocycle" or "heterocyclic", as used herein except where noted, represents a stable 4- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the examples and herein. Specific compounds within the present invention include a compound which selected from the group consisting of the compounds disclosed in the following examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of formula (I) with a pharmaceutical carrier or diluent.

The invention is also directed to the use of a compound of formula (I) for treating or preventing diseases in which the CGRP receptor is involved, such as migraine.

The invention is also directed to the use of a compound of formula (I), or a pharmaceutically acceptable salt thereof, and a pharmaceutically acceptable carrier, for the manufacture of a medicament for the treatment of a disease in which the CGRP receptor is involved.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25μ) were incubated in 1 ml of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 μl) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 μg/ml streptomycin at 37° C., 95% humidity, and 5% CO$_2$. For cAMP assays, cells were plated at 5×10$^5$ cells/well in 96-well poly-D-lysine-coated plates (Becton-Dickinson) and cultured for ~18 h before assay. Cells were washed with phosphate-buffered saline (PBS, Sigma) then pre-incubated with 300 μM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant (K$_i$)

determined by using a non-linear least squares fitting the bound CPM data to the equation below:

$$Y_{obsd} = \frac{Y_{min} + (Y_{max} - Y_{min})(100 - \% \, I_{max}/100) + (Y_{max} - Y_{min})(\% \, I_{max} - \%_{Imin}/100)}{1 + ([\text{Drug}]/K_i(1 + [\text{Radiolabel}]/K_d)^{nH}}$$

Where Y is observed CPM bound, $Y_{max}$ is total bound counts, Y min is non specific bound counts, (Y max–Y min) is specific bound counts, % I max is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The compounds of the present invention also have utility in treating, preventing, ameliorating, controlling or reducing the risk of one or more of the following conditions: thermal injury, circulatory shock, tumor growth, immune regulation in gut mucosa, modulation of bone resorption in bone disorders, airway inflammatory diseases and chronic obstructive pulmonary disease including asthma, and flushing associated with menopause.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a 5-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICY, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 10 milligrams to about 1000 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of some heterocyclic amine and acid intermediates may be conducted as described in Schemes 1-2. Related intermediates bearing a variety of substituents may be prepared by employing appropriately substituted starting materials or by derivatization of any intermediates and/or final products as desired by methods known in the art. Other intermediates of interest are described in a number of publications including, but not limited to, the following: Chaturvedula et al. WO 2006/052378; Bell et al. WO 2004/082605; Bell et al. WO 2004/082678; Bell et al. WO 2006/031513; Bell et al. WO 2006/031606; Bell et al. WO 2006/031610.

A representative synthesis of a spiroazaoxindole intermediate is shown in Scheme 1. The known pyridine diester 1 [Hashimoto et al. (1997) *Heterocycles* 46, 581] may be reduced to the corresponding diol 2 with lithium borohydride. This diol can be converted to the dibromide 3 by reaction with phosphorus tribromide in THF. 7-Azaindole (4) may be protected with a variety of protecting groups, such as the 2-(trimethylsilyl)ethoxymethyl group shown in Scheme 1. Following the method of Marfat and Carter [(1987) *Tetrahedron Lett.* 28, 4027], treatment of 5 with pyridine hydrobromide perbromide provides the dibromoazaoxindole 6, which may be reduced to the corresponding azaoxindole 7 by reaction with zinc. The key alkylation of 7 with dibromide 3 is carried out using cesium carbonate in DMF to afford the spiroazaoxindole 8. A variety of other bases and solvents may be employed in this alkylation reaction, and use of a different alkylating agent than the dibromide shown here can lead to other products. Treatment of compound 8 with aqueous HCl at reflux effects simultaneous hydrolysis of the nitrile and deprotection of the azaoxindole, affording the key acid intermediate 9. This carboxylic acid may be subjected to known Curtius rearrangement conditions to provide, after deprotection, aminopyridine 10. The methodology shown in Scheme 1 is not limited to azaoxindoles such as 7, but may be applied to a variety of suitably protected heterocyclic systems to give the corresponding Spiro compounds.

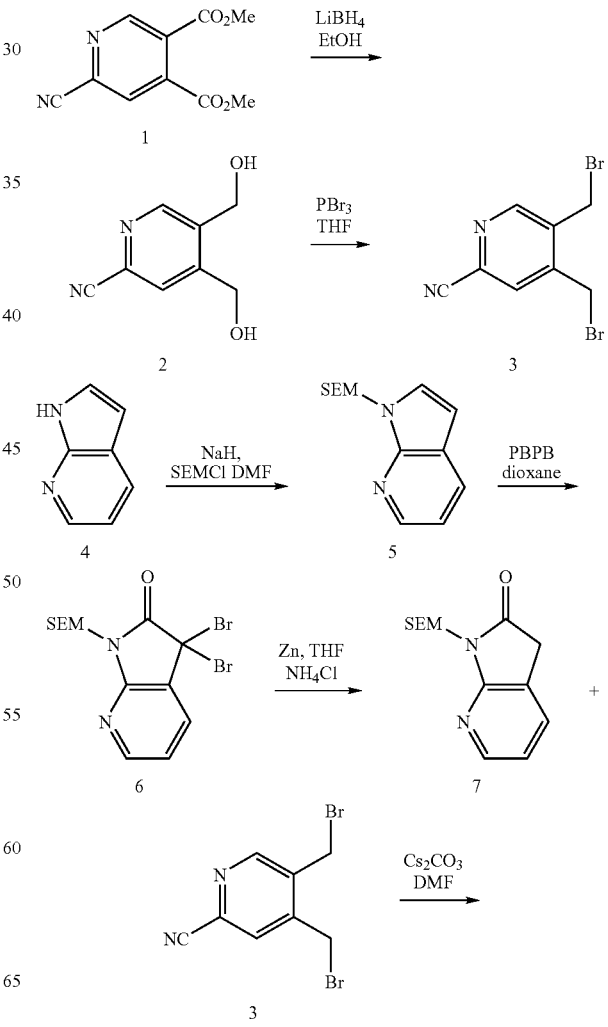

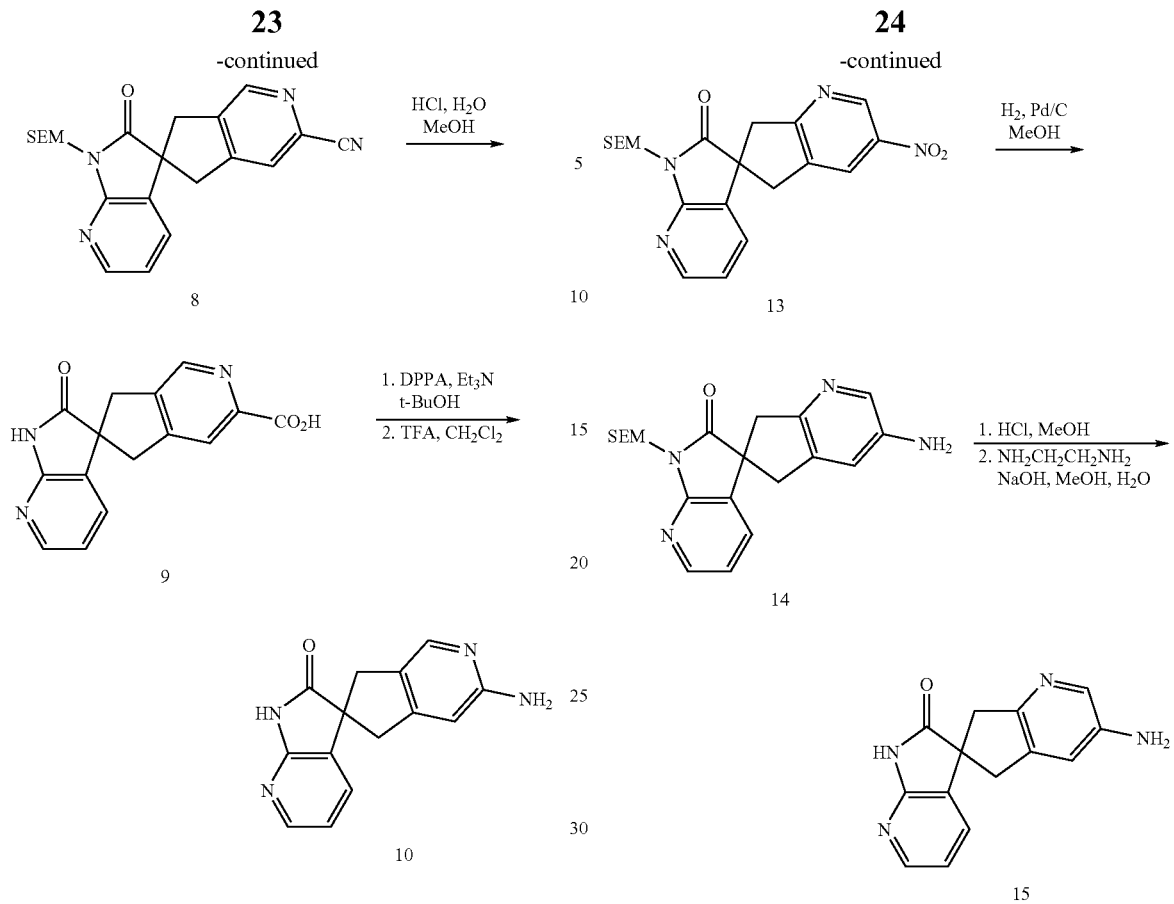

Scheme 2 illustrates a route to an isomer of compound 10, the 3-aminopyridine 15. Bis-alkylation of the spiroazaoxindole 7 with 1,4-dibromobutan-2-one [de Meijere et al. (2001) *Eur. J. Org. Chem.* 3789] provides the cyclopentanone 11. Condensation of ketone 11 with ammonia and 1-methyl-3,5-dinitropyridin-2(1H)-one [Tohda et al. (1990) *Bull. Chem. Soc. Japan* 63, 2820] in refluxing methanol leads to the 3-nitropyridine derivative 13. Catalytic hydrogenation may be used to provide the corresponding aniline 14. Standard deprotection of 14 using sequential acid and base treatments affords the 3-aminopyridine intermediate 15.

Spiroazaoxindole intermediates, such as those illustrated in Schemes 1 and 2, may be resolved to give pure enantiomers using techniques familiar to those skilled in the art. For example, chromatography of the suitable intermediates on a chiral column can be used to provide the individual stereoisomers. Resolution may also be effected by other methodologies, such as fractional crystallization of diastereomeric salts, and it may be carried out on other synthetic intermediates or on the final products. Alternatively, an asymmetric synthesis of a key intermediate could be used to provide an enantiomerically enriched final product.

A wide variety of intermediates may be reacted under conditions well known to those skilled in the art to provide the compounds of the present invention. For illustrative purposes, some examples of relevant methodology are shown in Scheme 3.

SCHEME 2

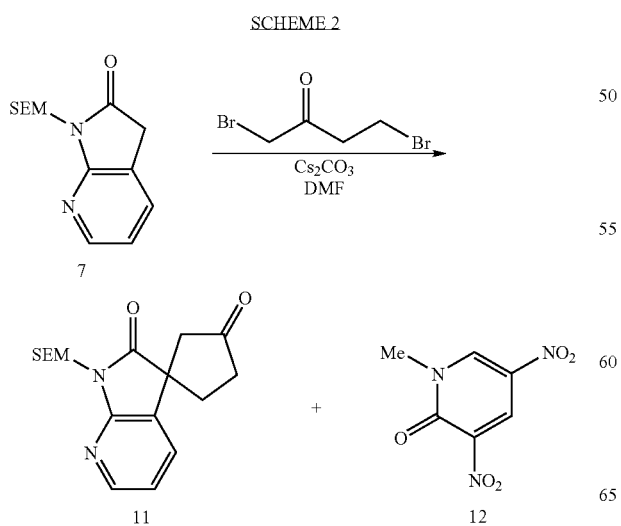

SCHEME 3

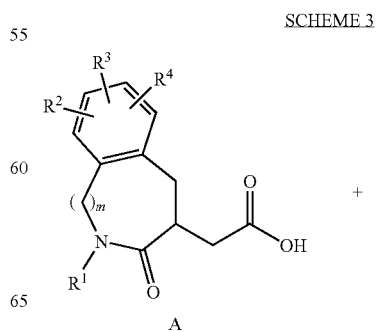

-continued

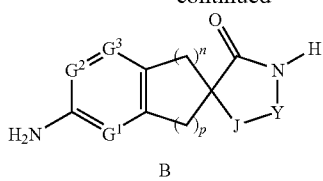
B

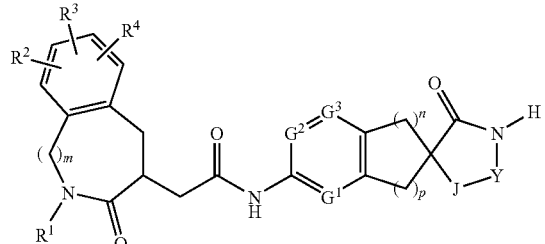
C

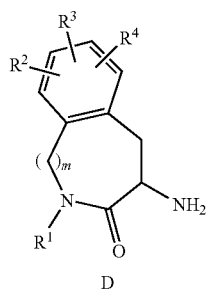
D

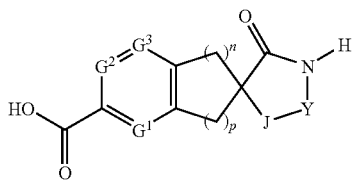
E

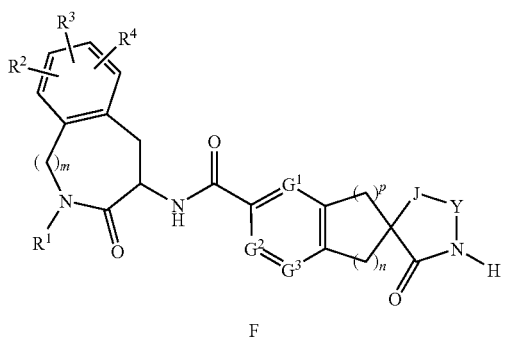
F

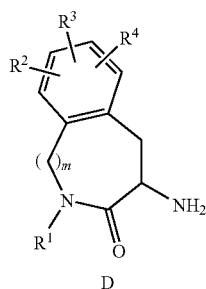
D

-continued

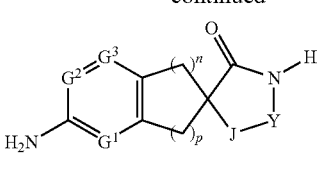
B

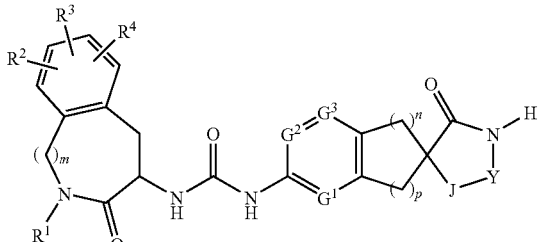
G

In Scheme 3, standard coupling of amines (e.g. B or D) with carboxylic acids (e.g. A or E) may be used to provide compounds of the present invention such as structures C and F. Such coupling reactions may be performed using a variety of known reagents and conditions. Examples include the use of EDC and HOBT in DMF, PyBOP in $CH_2Cl_2$, or HATU in DMF. Alternatively, the carboxylic acid may be activated, for example as the corresponding acid chloride or anhydride, to provide efficient reaction with amines of interest. In another example of the synthesis of compounds of the present invention, two amines, such as B and D, may be reacted with phosgene to give the urea G. Alternatives to phosgene, for example 1,1'-carbonyldiimidazole or 4-nitrophenylchloroformate, may also be effective in the formation of such ureas. The methodology illustrated in Scheme 3, as well as a wide variety of other transformations known to those skilled in the art of organic synthesis, may be used to synthesize compounds of the present invention.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

INTERMEDIATE 1

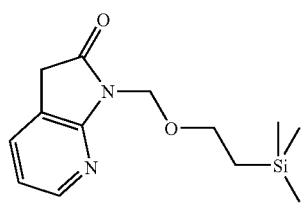

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc-90:10, to give the title compound. MS: m/z=265 (M+1).

INTERMEDIATE 2

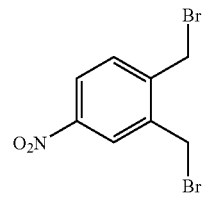

1,2-Bis(bromomethyl)-4-nitrobenzene

Step A. (4-Nitro-1,2-phenylene)dimethanol

A solution of 4-nitrophthalic acid (40 g, 189.5 mmol) in THF (500 mL) was added dropwise over 1.5 h to a solution of borane-THF complex (1 M, 490 mL, 490 mmol), keeping the reaction temperature between 0° C. and 5° C. After the addition, the reaction mixture was allowed to warm slowly to ambient temperature and stirred for 18 h. MeOH (100 mL) was added carefully and the precipitated solid dissolved. The mixture was concentrated in vacuo to about 500 mL, cooled to 0° C., and 10 N NaOH was added to adjust the pH to 10-11. This mixture was extracted with EtOAc (3×600 mL) and the combined organic layers were washed with brine, dried over $Na_2SO_4$, filtered, and concentrated in vacuo to give the title compound. MS: m/z=207 (M-OH+$CH_3CN$).

Step B. 1,2-Bis(bromomethyl)-4-nitrobenzene

Phosphorus tribromide (20.1 mL, 212 mmol) in $Et_2O$ (250 mL) was added dropwise over 1.5 h to a solution of (4-nitro-1,2-phenylene)dimethanol from Step A (35.3 g, 193 mmol) in $Et_2O$ (750 mL). After 18 h, the reaction mixture was cooled to 0° C. and quenched with $H_2O$ (100 mL). The layers were separated and the organic layer was washed with $H_2O$ (2×200 mL), then saturated aqueous $NaHCO_3$, dried over $Na_2SO_4$, filtered, and concentrated in vacuo to give the title compound. MS: m/z=309 (M+1).

INTERMEDIATE 3

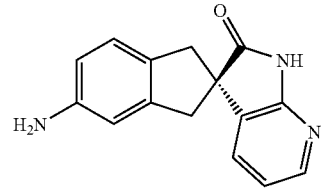

(R)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 2) and 1-{[2-(trimethylsilyl)ethoxy]methyl}-1,3-dihydro-2H-pyrrolo[2,3-b]pyridin-2-one (31.5 g, 119 mmol, described in Intermediate 1) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and H₂O (1 L). The organic layer was washed with H₂O (1 L), then brine (500 mL), then dried over Na₂SO₄, filtered, and concentrated in vacuo. The crude product was purified by silica gel chromatography, eluting with a gradient of hexane:EtOAc-100:0 to 0:100, to give the title compound. MS: m/z=412 (M+1).

Step B. (±)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the title compound. MS: m/z=382 (M+1).

Step C. tert-Butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate A solution of (±)-5-amino-1'-{[2-(trimethylsilyl)ethoxy]methyl}-1,3-dihydrospiro[indene-2,3'-b]pyridin]-2'(1'H)-one from Step B (104 g, 273 mmol) and di-tert-butyl dicarbonate (71.5 g, 328 mmol) in CHCl₃ (1 L) was heated to reflux for 17 h. The cooled mixture was concentrated in vacuo and the residue was purified by silica gel chromatography, eluting with hexane:EtOAc-100:0 to 50:50, to give the racemic product. The enantiomers were resolved by HPLC, utilizing a ChiralPak AD column and eluting with EtOH. The first major peak to elute was tert-butyl(S)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, and the second major peak to elute was tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, the title compound. MS: m/z=482 (M+1).

Step D. (R)-5-Amino-1,3-dihydrospiro[indene-2,3'-pyrrolo[2,3-b]pyridin]-2'(1'H)-one A solution of tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate from Step C (13.4 g, 27.8 mmol) in MeOH (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (1.9 mL, 27.8 mmol) and 10 N sodium hydroxide (6 mL, 60 mmol) to adjust the mixture to pH 10. After 30 min, the mixture was diluted with H₂O (400 mL) and extracted with CHCl₃ (1 L). The organic layer was dried over Na₂SO₄, filtered, and concentrated in vacuo. The crude material was triturated with MeOH (35 mL) to give the title compound. MS: m/z=252 (M+1).

INTERMEDIATE 4

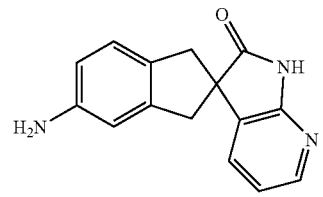

(±)-5-Amino-1,3-dihydrospiro[indene-2,3'-pyrrolo[2,3-b]pyridin]-2'(1'H)-one

Essentially following the procedures described for Intermediate 3, but using (±)-5-amino-1'-{[2-(trimethylsilyl)ethoxy]methyl}-1,3-dihydrospiro[indene-2,3'-pyrrolo[2,3-b]pyridin]-2'(1'H)-one (described in Intermediate 3) in place of tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, the title compound was obtained. MS: m/z=252 (M+1).

INTERMEDIATE 5

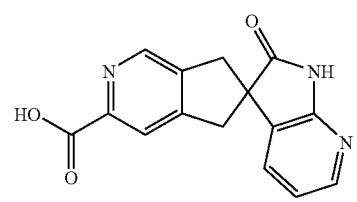

(±)-2'-Oxo-1',2',5,7-tetrahydrospiro[cyclopenta[c]pyridine-6,3'-pyrrolo[2,3-b]pyridine]-3-carboxylic acid hydrochloride Step A. 4,5-Bis(hydroxymethyl)pyridine-2-carbonitrile To a solution of dimethyl 6-cyanopyridine-3,4-dicarboxylate (2.00 g, 9.08 mmol) [Hashimoto et al. (1997) *Heterocycles* 46, 581] in EtOH (50 mL) was added lithium borohydride (4.54 mL of a 2 M solution in THF, 9.08 mmol) dropwise. The reaction mixture was stirred at ambient temperature for 3 h, and then cooled to 0° C. Saturated aqueous NaHCO₃ (20 mL) was added slowly and the quenched mixture was extracted with EtOAc (9×100 mL). The combined organic extracts were dried over Na₂SO₄, filtered, and concentrated in vacuo. The crude product was purified by silica gel chromatography, eluting with a gradient of CH₂Cl₂:MeOH-100:0 to 85:15, to give the title compound. MS: m/z=165 (M+1).

Step B. 4,5-Bis(bromomethyl)pyridine-2-carbonitrile

To a solution of 4,5-bis(hydroxymethyl)pyridine-2-carbonitrile from Step A (750 mg, 4.57 mmol) in THF (15 mL) was added phosphorus tribromide (1.61 g, 5.94 mmol) in THF (5 mL) dropwise. The reaction mixture was stirred at ambient temperature for 2 h, and then cooled to 0° C. Saturated aqueous NaHCO₃ (5 mL) was added slowly and the quenched mixture was extracted with CHCl₃ (2×30 mL). The combined organic extracts were dried over Na₂SO₄, filtered, and concentrated in vacuo. The crude product was purified by silica gel chromatography, eluting with a gradient of hexane: EtOAc-100:0 to 27:75, to give the title compound. MS: m/z=291 (M+1).

Step C. (±)-2'-Oxo-1'-{[2-(trimethylsilyl)ethoxy] methyl}-1',2',5,7-tetrahydrospiro[cyclopenta[c]pyridine-6,3'-pyrrolo[2,3-b]pyridine]-3-carbonitrile To a solution of 4,5-bis(bromomethyl)pyridine-2-carbonitrile from Step B (729 mg, 2.52 mmol) and 1-{[2-(trimethylsilyl)ethoxy]methyl}-1,3-dihydro-2H-pyrrolo[2,3-b]pyridin-2-one (665 mg, 2.52 mmol, described in Intermediate 1) in DMF (75 mL) was added cesium carbonate (2.46 g, 7.55 mmol), portionwise, over 5 min. After 2 h, acetic acid (0.15 mL) was added and the mixture was concentrated to a volume of about 25 mL, then partitioned between $CHCl_3$ (100 mL), saturated aqueous $NaHCO_3$ (30 mL) and brine (50 mL). The organic layer was removed and the aqueous layer was extracted further with $CHCl_3$ (100 mL). The combined organic extracts were dried over $Na_2SO_4$, filtered, and concentrated in vacuo. The crude product was purified by silica gel chromatography, eluting with a gradient of hexane: EtOAc-100:0 to 0:100, to give the title compound. MS: m/z=393 (M+1).

Step D. (±)-2'-Oxo-1',2',5,7-tetrahydrospiro[cyclopenta[c]pyridine-6,3'-pyrrolo[2,3-b]pyridine]-3-carboxylic acid hydrochloride To a solution of (±)-2'-oxo-1'-{[2-(trimethylsilyl)ethoxy] methyl}-1',2',5,7-tetrahydrospiro[cyclopenta[c]pyridine-6, 3'-pyrrolo[2,3-b]pyridine]-3-carbonitrile from Step C (6.10 g, 15.5 mmol) in THF (30 mL) was added 3 N aqueous HCl (360 mL). The mixture was heated at reflux for 18 h, allowed to cool and concentrated to dryness in vacuo. The residue was redissolved in 3 N aqueous HCl (360 mL) and heated at reflux for 18 h. The cooled mixture was concentrated to dryness in vacuo to afford the title compound in sufficient purity for use in subsequent steps. MS: m/z=282 (M+1).

INTERMEDIATE 6

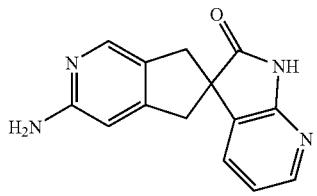

(±)-3-Amino-5,7-dihydrospiro[cyclopenta[c]pyridine-6,3'-pyrrolo[2,3-b]pyridin]-2'(1'H)-one Step A. (±)-tert-Butyl (2'-oxo-1',2',5,7-tetrahydrospiro[cyclopenta[c]pyridine-6,3'-pyrrolo[2,3-b] pyridin]-3-yl)carbamate To a refluxing suspension of (±)-2'-oxo-1',2',5,7-tetrahydrospiro[cyclopenta[c]pyridine-6,3'-pyrrolo[2,3-b]pyridine]-3-carboxylic acid (200 mg, 0.711 mmol, described in Intermediate 5) and triethylamine (0.149 mL, 1.07 mmol) in tert-butanol (10 mL) was added diphenylphosphoryl azide (0.184 mL, 0.853 mmol). After 18 h at reflux, the mixture was concentrated in vacuo. The residue was partitioned between $CH_2Cl_2$ (50 mL) and saturated $NaHCO_3$ (30 mL) The organic layer was separated and the aqueous layer was further extracted with $CH_2Cl_2$ (2×50 mL). The combined organic layers were dried over $Na_2SO_4$, filtered, and concentrated in vacuo. The crude product was purified by silica gel chromatography, eluting with a gradient of $CH_2Cl_2$:MeOH: $NH_4OH$-100:0:0 to 95:5:1, to give the title compound. MS: m/z=353 (M+1).

Step B. (±)-3-Amino-5,7-dihydrospiro[cyclopenta[c] pyridine-6,3'-pyrrolo[2,3-b]pyridin]-2'(1'H)-one trifluoroacetate A solution of (±)-tert-butyl (2'-oxo-1',2',5,7-tetrahydrospiro[cyclopenta[c]pyridine-6,3'-pyrrolo[2,3-b]pyridin]-3-yl)carbamate from Step A (131 mg, 0.372 mmol) was stirred in $CH_2Cl_2$ (10 mL) and TFA (3 mL) for 18 h and then concentrated in vacuo to provide the title compound. MS: m/z=253 (M+1).

INTERMEDIATE 7

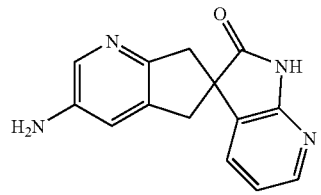

(±)-3-Amino-5,7-dihydrospiro[cyclopenta[b]pyridine-6,3'-pyrrolo[2,3-b]pyridin]-2'(1'H)-one trifluoroacetate Step A. (±)-1'-{[2-(Trimethylsilyl)ethoxy]methyl}-3H-spiro[cyclopentane-1,3'-pyrrolo[2,3-b]pyridine]-2',3(1'H)-dione To a solution of 1-{[2-(trimethylsilyl)ethoxy]methyl}-1,3-dihydro-2H-pyrrolo[2,3-b]pyridin-2-one (2.50 g, 9.46 mmol, described in Intermediate 1) and cesium carbonate (6.78 g, 20.8 mmol) in DMF (45 mL) was added dropwise a solution of 1,4-dibromobutan-2-one (1.59 mL, 12.3 mmol) [de Meijere et al. (2001) *Eur. J. Org. Chem.* 3789] in DMF (45 mL). After 68 h, the mixture was partitioned between $Et_2O$ (200 mL) and $H_2O$ (200 mL). The organic layer was separated and the aqueous layer was further extracted with $Et_2O$ (2×100 mL). The combined organic layers were dried over $Na_2SO_4$, filtered, and concentrated in vacuo. The crude product was purified by silica gel chromatography, eluting with a gradient of hexane:EtOAc-100:0 to 75:25, to give the title compound. MS: m/z=333 (M+1).

Step B. (±)-3-Nitro-1'-{[2-(trimethylsilyl)ethoxy] methyl}-5,7-dihydrospiro[cyclopenta[b]pyridine-6, 3'-pyrrolo[2,3-b]pyridin]-2'(1'H)-one A mixture of (±)-1'-{[2-(trimethylsilyl)ethoxy]methyl}-3H-spiro[cyclopentane-1,3'-pyrrolo[2,3-b]pyridine]-2',3 (1'H)-dione from Step A (230 mg, 0.692 mmol) and 1-methyl-3,5-dinitropyridin-2(1H)-one (173 mg, 0.869 mmol) [Tohda et al. (1990) *Bull. Chem. Soc. Japan* 63, 2820] in 2 M ammonia in MeOH (3.5 mL) was heated to reflux for 18 h. The mixture was concentrated in vacuo and purified by silica gel chromatography, eluting with a gradient of hexane: EtOAc-100:0 to 50:50, to give the title compound. MS: m/z=413 (M+1).

Step C. (±)-3-Amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of 10% Pd/C (20 mg) and (±)-3-nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step B (117 mg, 0.284 mmol) was stirred vigorously in MeOH (5 mL) under an atmosphere of hydrogen (ca. 1 atm). After 4.5 h, the mixture was filtered through a pad of Celite, washing extensively with MeOH, and the filtrate was concentrated in vacuo to give the title compound. MS: m/z=383 (M+1).

Step D. (±)-3-Amino-5,7-dihydrospiro[cyclopenta[b]pyridine-6,3'-pyrrolo[2,3-b]pyridin]-2'(1'H)-one trifluoroacetate A solution of (±)-3-amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step C (117 mg, 0.306 mmol) in MeOH (5 mL) was saturated with HCl (g). The mixture was stirred for 30 min and then concentrated in vacuo. The residue was dissolved in MeOH (3 mL), treated with ethylenediamine (0.020 mL, 0.306 mmol), and 10 N sodium hydroxide was added to adjust the mixture to pH 10. After 1 h, the reaction mixture was purified directly by HPLC using a reversed phase C18 column and eluting with a gradient of $H_2O:CH_3CN:CF_3CO_2H$-90:10:0.1 to 5:95:0.1. MS: m/z=253 (M+1).

Example 1

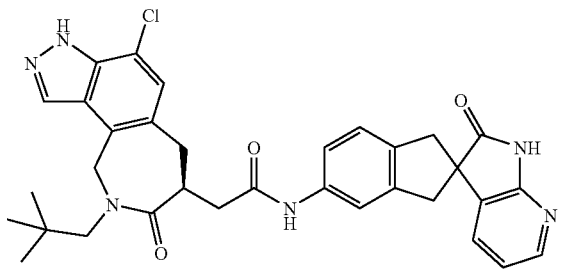

2-[(7S)-4-Chloro-9-(2,2-dimethylpropyl)-8-oxo-3,6,7,8,9,10-hexahydroazepino[3,4-e]indazol-7-yl]-N-(2'-oxo-1,1',2',3-tetrahydrospiro[indene-2,3'-pyrrolo[2,3-b]pyridin]-5-yl)acetamide A mixture of [4-chloro-9-(2,2-dimethylpropyl)-8-oxo-3,6,7,8,9,10-hexahydro-2,3,9-triaza-(S)-cyclohepta[e]inden-7-yl]acetic acid (85 mg, 0.23 mmol) [Chaturvedula et al. WO 2006/052378], (±)-5-amino-1,3-dihydrospiro[indene-2,3'-pyrrolo[2,3-b]pyridin]-2'(1'H)-one (70 mg, 0.28 mmol, described in Intermediate 4), HOBT (43 mg, 0.28 mmol), and EDC (54 mg, 0.28 mmol) in DMF (2 mL) is stirred at ambient temperature for 18 h. The reaction mixture is purified directly by HPLC using a reversed phase C18 column and eluting with a gradient of $H_2O:CH_3CN:CF_3CO_2H$-90:10:0.1 to 5:95:0.1. The pure, product-containing fractions are combined and made basic with saturated aqueous $NaHCO_3$. The resulting mixture is extracted with EtOAc (2×20 mL), and the combined organic extracts are washed with brine, dried over $Na_2SO_4$, filtered, and concentrated in vacuo to provide the title compound.

Example 2

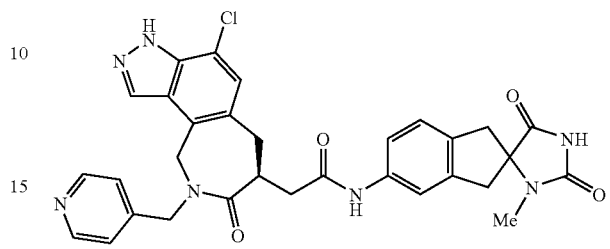

2-[(7S)-4-Chloro-8-oxo-9-(pyridin-4-ylmethyl)-3,6,7,8,9,10-hexahydroazepino[3,4-e]indazol-7-yl]-N-(3-methyl-2,5-dioxo-1',3'-dihydrospiro[imidazolidine-4,2'-inden]-5'-yl)acetamide A mixture of (S)-2-[4-chloro-8-oxo-9-(pyridine-4-ylmethyl)-3,6,7,8,9,10-hexahydroazepino[3,4-e]indazol-7-yl] acetic acid dihydrochloride (105 mg, 0.23 mmol) [Chaturvedula et al. WO 2006/052378], (±)-5'-amino-3-methyl-spiro[imidazolidine-4,2'-indane]-2,5-dione (65 mg, 0.28 mmol) [Bell et al. WO 2004/082605], HOBT (43 mg, 0.28 mmol), and EDC (54 mg, 0.28 mmol) in DMF (2 mL) is stirred at ambient temperature for 18 h. The reaction mixture is purified directly by HPLC using a reversed phase C18 column and eluting with a gradient of $H_2O:CH_3CN:CF_3CO_2H$-90:10:0.1 to 5:95:0.1. The pure, product-containing fractions are combined and made basic with saturated aqueous $NaHCO_3$. The resulting mixture is extracted with EtOAc (2×20 mL), and the combined organic extracts are washed with brine, dried over $Na_2SO_4$, filtered, and concentrated in vacuo to provide the title compound.

Example 3

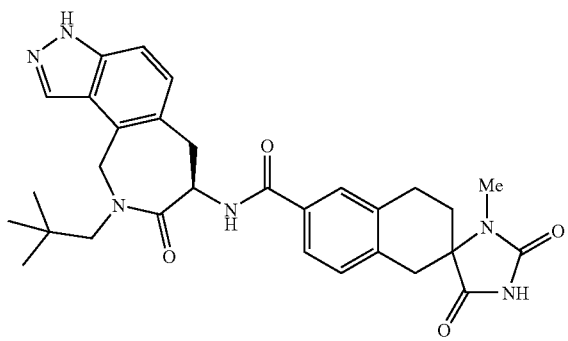

N-[(7R)-9-(2,2-Dimethylpropyl)-8-oxo-3,6,7,8,9,10-hexahydroazepino[3,4-e]indazol-7-yl]-3-methyl-2,5-dioxo-3',4'-dihydro-1'H-spiro[imidazolidine-4,2'-naphthalene]-6'-carboxamide A mixture of 7-(R)-amino-9-(2,2-dimethylpropyl)-6,7,9,10-tetrahydro-3H-2,3,9-triazacyclohepta[e]inden-8-one bis-methanesulfonate (110 mg, 0.23 mmol) [Chaturvedula et al. WO 2006/052378], (±)-3-methyl-2,5-dioxo-3',4'-dihydro-1'H-spiro[imidazolidine-4,2'-naphthalene]-6'-carboxylic acid (77 mg, 0.28 mmol) [Bell et al. WO 2004/082605], HOBT (43 mg, 0.28 mmol), and EDC (54 mg, 0.28 mmol) in DMF (2 mL) is stirred at ambient temperature for 18 h. The reaction mixture is purified directly by HPLC using a reversed phase C18 column and eluting with a gradient of $H_2O:CH_3CN:CF_3CO_2H$-90:10:0.1 to 5:95:0.1. The pure, product-containing fractions are combined and made basic with saturated aqueous $NaHCO_3$. The resulting mixture is extracted with EtOAc (2×20 mL), and the combined organic extracts are washed with brine, dried over $Na_2SO_4$, filtered, and concentrated in vacuo to provide the title compound.

Example 4

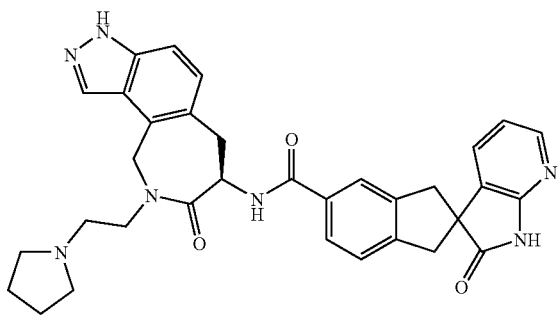

2'-Oxo-N-[(7R)-8-oxo-9-(2-pyrrolidin-1-ylethyl)-3,6,7,8,9,10-hexahydroazepino[3,4-e]indazol-7-yl]-1,1',2',3-tetrahydrospiro[indene-2,3'-pyrrolo[2,3-b]pyridine]-5-carboxamide A mixture of 7-(R)-amino-9-(2-pyrrolidin-1-yl-ethyl)-6,7,9,10-tetrahydro-3H-2,3,9-triazacyclohepta[e]inden-8-one (72 mg, 0.23 mmol) [Chaturvedula et al. WO 2006/052378], (±)-2'-oxo-1,1',2',3-tetrahydrospiro[indene-2,3'-pyrrolo[2,3-b]pyridine]-5-carboxylic acid (78 mg, 0.28 mmol) [Bell et al. WO 2006/031606], HOBT (43 mg, 0.28 mmol), and EDC (54 mg, 0.28 mmol) in DMF (2 mL) is stirred at ambient temperature for 18 h. The reaction mixture is purified directly by HPLC using a reversed phase C18 column and eluting with a gradient of $H_2O:CH_3CN:CF_3CO_2H$-90:10:0.1 to 5:95:0.1. The pure, product-containing fractions are combined and made basic with saturated aqueous $NaHCO_3$. The resulting mixture is extracted with EtOAc (2×20 mL), and the combined organic extracts are washed with brine, dried over $Na_2SO_4$, filtered, and concentrated in vacuo to provide the title compound.

Example 5

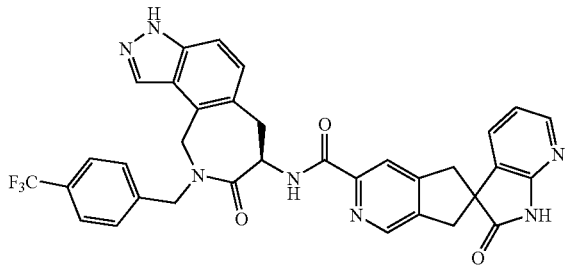

2'-Oxo-N-{(7R)-8-oxo-9-[4-(trifluoromethyl)benzyl]-3,6,7,8,9,10-hexahydroazepino[3,4-e]indazol-7-yl}-1',2',5,7-tetrahydrospiro[cyclopenta[c]pyridine-6,3'-pyrrolo[2,3-b]pyridine]-3-carboxamide A mixture of 7-(R)-amino-9-(4-trifluoromethylbenzyl)-6,7,9,10-tetrahydro-3H-2,3,9-triazacyclohepta[e]inden-8-one (86 mg, 0.23 mmol) [Chaturvedula et al. WO 2006/052378], (±)-2'-oxo-1',2',5,7-tetrahydrospiro[cyclopenta[c]pyridine-6,3'-pyrrolo[2,3-b]pyridine]-3-carboxylic acid (79 mg, 0.28 mmol, described in Intermediate 5), HOBT (43 mg, 0.28 mmol), and EDC (54 mg, 0.28 mmol) in DMF (2 mL) is stirred at ambient temperature for 18 h. The reaction mixture is purified directly by HPLC using a reversed phase C18 column and eluting with a gradient of $H_2O:CH_3CN:CF_3CO_2H$-90:10:0.1 to 5:95:0.1. The pure, product-containing fractions are combined and made basic with saturated aqueous $NaHCO_3$. The resulting mixture is extracted with EtOAc (2×20 mL), and the combined organic extracts are washed with brine, dried over $Na_2SO_4$, filtered, and concentrated in vacuo to provide the title compound.

Example 6

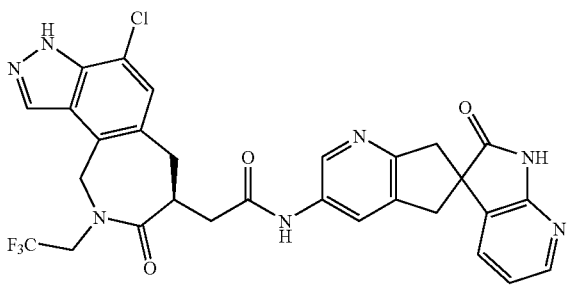

2-[(7S)-4-Chloro-8-oxo-9-(2,2,2-trifluoroethyl)-3,6,7,8,9,10-hexahydroazepino[3,4-e]indazol-7-yl]-N-(2'-oxo-1',2',5,7-tetrahydrospiro[cyclopenta[b]pyridine-6,3'-pyrrolo[2,3-b]pyridin]-3-yl)acetamide A mixture of [4-chloro-3,6,7,8,9,10-hexahydro-8-oxo-9-(2,2,2-trifluoroethyl)-2,3,9-triaza-(S)-cyclohepta[e]inden-7-yl]acetic acid (86 mg, 0.23 mmol) [Chaturvedula et al. WO 2006/052378], (±)-3-amino-5,7-dihydrospiro[cyclopenta[b]
pyridine-6,3'-pyrrolo[2,3-b]pyridin]-2'(1'H)-one (71 mg,
0.28 mmol, described in Intermediate 7), HOBT (43 mg, 0.28
mmol), and EDC (54 mg, 0.28 mmol) in DMF (2 mL) is
stirred at ambient temperature for 18 h. The reaction mixture
is purified directly by HPLC using a reversed phase C18
column and eluting with a gradient of $H_2O:CH_3CN:CF_3CO_2H$-90:10:0.1 to 5:95:0.1. The pure, product-containing fractions are combined and made basic with saturated
aqueous $NaHCO_3$. The resulting mixture is extracted with
EtOAc (2×20 mL), and the combined organic extracts are
washed with brine, dried over $Na_2SO_4$, filtered, and concentrated in vacuo to provide the title compound.

Example 7

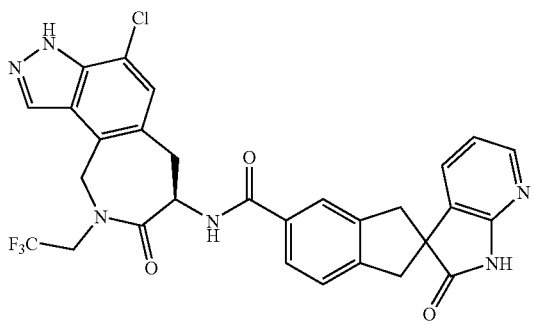

N-[(7R)-4-Chloro-8-oxo-9-(2,2,2-trifluoroethyl)-3,6,
7,8,9,10-hexahydroazepino[3,4-e]indazol-7-yl]-2'-
oxo-1,1',2',3-tetrahydrospiro[indene-2,3'-pyrrolo[2,3-
b]pyridine]-5-carboxamide Step A. Benzyl[(7R)-4-chloro-8-oxo-9-(2,2,2-trifluoroethyl)-3,6,7,8,9,10-hexahydroazepino[3,4-e]indazol-7-yl]carbamate A mixture of 2-(R)-benzyloxycarbonylamino-3-(7-chloro-4-chloromethyl-1H-indazol-5-yl)propionic acid methyl ester
(525 mg, 1.20 mmol) [Chaturvedula et al. WO 2006/052378],
trifluoroethylamine (1.0 g, 10.2 mmol), and $K_2CO_3$ (499 mg,
3.61 mmol) in CH3CN (15 mL) was heated at 40° C. in a
sealed vessel for 45 h. Additional trifluoroethylamine (1.0 g,
10.2 mmol) was added and the mixture was heated at 40° C.
for a further 48 h and then allowed to cool to ambient temperature. The reaction mixture was filtered through a 0.45 μm
PTFE membrane and the filtrate was concentrated in vacuo.
The residue was dissolved in toluene (10 mL) and AcOH (1
mL) and the mixture was heated at reflux for 6 h, allowed to
cool to ambient temperature, and partitioned between saturated aqueous NaHCO3 (30 mL) and EtOAc (60 mL). The
organic layer was washed with brine, dried over $Na_2SO_4$,
filtered, and concentrated in vacuo. The crude product was
purified by silica gel chromatography, eluting with a gradient
of $CH_2Cl_2$:EtOAc-100:0 to 50:50, to provide the title compound. MS: m/z=467.

Step B. (7R)-7-Amino-4-chloro-9-(2,2,2-trifluoroethyl)-6,7,9,10-tetrahydroazepino[3,4-e]indazol-8
(3H)-one bis-methanesulfonate To a mixture of benzyl[(7R)-4-chloro-8-oxo-9-(2,2,2-trifluoroethyl)-3,6,7,8,9,10-hexahydroazepino[3,4-e]indazol-7-yl]carbamate from Step A (265 mg, 0.568 mmol) and anisole
(184 mg, 1.70 mmol) in $CH_2Cl_2$ (4 mL) was added methanesulfonic acid (1.84 mL, 28 mmol). The resulting mixture was
stirred at ambient temperature for 45 min, $Et_2O$ (45 mL) was
added, and stirring was continued for 20 min. The supernatant
was removed and the residue was washed with $Et_2O$ and dried
in vacuo to give the title compound. MS: m/z=333.

Step C. N-[(7R)-4-Chloro-8-oxo-9-(2,2,2-trifluoroethyl)-3,6,7,8,9,10-hexahydroazepino[3,4-e]indazol-7-
yl]-2'-oxo-1,1',2',3-tetrahydrospiro[indene-2,3'-pyrrolo[2,3-b]pyridine]-5-carboxamide A mixture of (7R)-7-amino-4-chloro-9-(2,2,2-trifluoroethyl)-6,7,9,10-tetrahydroazepino[3,4-e]indazol-8(3H)-one
bis-methanesulfonate from Step B (20 mg, 0.038 mmol),
(±)-2'-oxo-1,1',2',3-tetrahydrospiro[indene-2,3'-pyrrolo[2,3-
b]pyridine]-5-carboxylic acid (11 mg, 0.038 mmol) [Bell et
al. WO 2006/031606], N,N-diisopropylethylamine (25 mg,
33 uL, 0.19 mmol), HOBT (7.0 mg, 0.046 mmol), and EDC
(8.8 mg, 0.046 mmol) in DMF (0.5 mL) was stirred at ambient
temperature for 2 h. The reaction mixture was purified
directly by HPLC using a reversed phase C18 column and
eluting with a gradient of $H_2O:CH_3CN:CF_3CO_2H$-90:10:0.1
to 5:95:0.1. The pure, product-containing fractions were concentrated in vacuo to provide the title compound. MS:
m/z=595.

Example 8

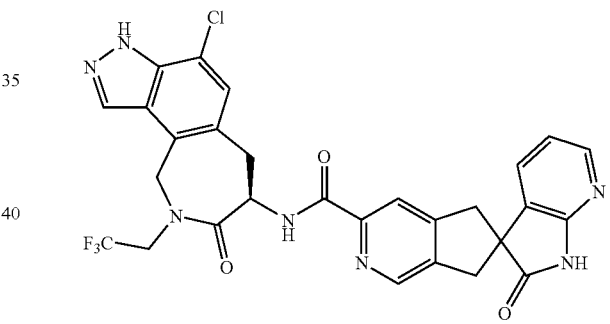

N-[(7R)-4-Chloro-8-oxo-9-(2,2,2-trifluoroethyl)-3,6,
7,8,9,10-hexahydroazepino[3,4-e]indazol-7-yl]-2'-
oxo-1',2',5,7-tetrahydrospiro[cyclopenta[c]pyridine-
6,3'-pyrrolo[2,3-b]pyridine]-3-carboxamide A mixture of (7R)-7-amino-4-chloro-9-(2,2,2-trifluoroethyl)-6,7,9,10-tetrahydroazepino[3,4-e]indazol-8(3H)-one
bis-methanesulfonate (16 mg, 0.030 mmol, described in
Example 7, Step B), (±)-2'-oxo-1',2',5,7-tetrahydrospiro[cyclopenta[c]pyridine-6,3'-pyrrolo[2,3-b]pyridine]-3-carboxylic acid (8.6 mg, 0.030 mmol, described in Intermediate 5),
N,N-diisopropylethylamine (20 mg, 27 uL, 0.15 mmol),
HOBT (5.6 mg, 0.037 mmol), and EDC (7.0 mg, 0.037 mmol)
in DMF (0.5 mL) was stirred at ambient temperature for 18 h.
The reaction mixture was purified directly by HPLC using a
reversed phase C18 column and eluting with a gradient of
$H_2O:CH_3CN:CF_3CO_2H$-90:10:0.1 to 5:95:0.1. The pure,
product-containing fractions were concentrated in vacuo to
provide the title compound. MS: m/z=596.

Although specific enantiomers and diastereomers appear
in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diasteriomer subsequent to a chiral resolution) will provide alternative enantiomers and diastereomers, all of which are included in the spirit and scope of the invention. It is intended that all of the possible optical isomers and diastereomers in mixtures and as pure or partially purified compounds are included within the ambit of this invention. The present invention is meant to comprehend all such isomeric forms of these compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

I wherein:
- $R^1$ is selected from $C_{1-6}$alkyl, $C_{2-6}$alkenyl, $C_{3-7}$cycloalkyl, $C_{5-7}$cycloalkenyl, $C_{1-6}(C_{3-7}$cycloalkyl)alkyl, $C_{1-6}$haloalkyl, $C_{1-6}(C_{1-6}$alkoxy)alkyl, $C_{1-6}(Ar^1)$alkyl, $C_{1-6}(NR^7R^8)$alkyl, N—$(R^{16})$-pyrrolidinyl and N—$(R^{16})$-piperidinyl;
- $R^2$ and $R^3$ are on adjacent carbon atoms and together form —C(H)=N—N($R^9$)—, thereby forming a fused ring;
- $R^4$ is hydrogen, halo, $C_{1-6}$alkyl, or $C_{2-6}$alkenyl;
- $R^7$ is hydrogen or $C_{1-6}$alkyl;
- $R^8$ is hydrogen or $C_{1-6}$alkyl;
- or $NR^7R^8$ join to form a ring selected from the group consisting of pyrrolidinyl, piperidinyl, N—$(R^{16})$-piperazinyl, morpholinyl, and thiomorpholinyl;
- $R^{16}$ is hydrogen, $C_{1-6}$alkyl, $C_{1-6}$alkylcarbonyl, or $C_{1-6}$alkoxycarbonyl;
- $Ar^1$ is phenyl, naphthyl, pyridinyl, or imidazolyl, where $Ar^1$ is substituted with 0-2 substituents selected from the group consisting of halo, $C_{1-6}$alkyl, $C_{1-6}$haloalkyl,
- $A^1$, $A^2$ and $A^3$ are each independently selected from:
  (1) a bond,
  (2) —$CR^{13}R^{14}$—,
  (3) —C(=O)—,
  (4) —O—,
  (5) —N($R^9$)—, or
  (6) —C(=N—CN)—,
  wherein one or two of $A^1$, $A^2$ and $A^3$ are optionally absent;
- $G^1$, $G^2$ and $G^3$ are each independently selected from:
  (1) —C($R^5$)=,
  (2) —N=, and
  (3) —($N^+$—$O^-$)=;
- J is independently selected from:
  (1) =C($R^{6a}$)—,
  (2) —$CR^{13}R^{14}$—,
  (3) —C(=O)—, and
  (4) —N($R^{15}$)—;
- Y is independently selected from:
  (1) =C($R^{6b}$)—,
  (2) —$CR^{13}R^{14}$—,
  (3) —C(=O)—,
  (4) —$SO_2$—,
  (5) =N—, and
  (6) —N($R^{6b}$)—;
- $R^5$ is independently selected from:
  (1) hydrogen,
  (2) $C_{1-6}$alkyl,
  (3) —O—$C_{1-6}$alkyl,
  (4) —$OCF_3$,
  (5) trifluoromethyl,
  (6) halo,
  (7) hydroxy, and
  (8) —CN;
- $R^{6a}$ and $R^{6b}$ are each independently selected from:
  (1) hydrogen;
  (2) —$C_{1-4}$alkyl, which is unsubstituted or substituted with 1-5 substituents each independently selected from:
    (a) halo,
    (b) —O—$C_{3-6}$alkyl,
    (c) —$C_{3-6}$cycloalkyl,
    (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl and morpholinyl, which phenyl or heterocycle is unsubstituted or substituted with 1-3 substituents each independently selected from:
      (i) —$C_{1-6}$alkyl,
      (ii) —O—$C_{1-6}$alkyl,
      (iii) halo,
      (iv) hydroxy,
      (v) trifluoromethyl, and
      (vi) —$OCF_3$,
  (3) phenyl or heterocycle, wherein said heterocycle is selected from: pyridyl, pyrimidinyl, pyrazinyl, thienyl, pyrrolidinyl, azetidinyl, thiazolyl, oxazolyl, imidazolyl, triazolyl, tetrahydrofuryl, piperidinyl and morpholinyl, which phenyl or heterocycle is unsubstituted or substituted with 1-3 substituents where each independently selected from:

(a) —$C_{1-4}$alkyl, which is unsubstituted or substituted with 1-5 fluoro,
(b) halo,
(c) hydroxy,
(d) —O—$C_{1-4}$alkyl, which is unsubstituted or substituted with 1-5 fluoro,
(e) —$C_{3-6}$cycloalkyl, and
(f) phenyl,
(4) halo,
(5) hydroxy,
(6) —O—$C_{1-6}$alkyl, which is unsubstituted or substituted with 1-5 halo,
(7) —CN,
(8) —$CO_2R^9$,
(9) —$NR^{10}R^{11}$, and
(10) —$CONR^{10a}R^{11a}$;
or where $R^{6a}$ and $R^{6b}$ join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) hydroxy,
    (iii) —O—$C_{1-6}$alkyl,
    (iv) —$C_{3-6}$cycloalkyl,
    (v) phenyl or heterocycle, wherein said heterocycle is selected from: pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$C_{1-6}$alkyl,
      (II) —O—$C_{1-6}$alkyl,
      (III) halo,
      (IV) hydroxy,
      (V) trifluoromethyl, and
      (VI) —$OCF_3$,
      (VI) —$CO_2R^9$,
      (VII) —$NR^{10}R^{11}$,
      (VIII) —$SO_2R^{12}$,
      (IX) —$CONR^{10a}R^{11a}$, and
      (X) —$(NR^{10a})CO_2R^9$,
  (b) phenyl or heterocycle, wherein said heterocycle is selected from: pyridyl, pyrimidinyl, pyrazinyl, thienyl, pyridazinyl, pyrrolidinyl, azetidinyl, piperidinyl and morpholinyl, which phenyl or heterocycle is unsubstituted or substituted with 1-3 substituents each independently selected from:
    (i) —$C_{1-6}$alkyl, which is unsubstituted or substituted with 1-6 fluoro,
    (ii) halo,
    (iii) hydroxy,
    (iv) —O—$C_{1-6}$alkyl, which is unsubstituted or substituted with 1-6 fluoro, and
    (v) —$C_{3-6}$cycloalkyl,
  (c) halo,
  (d) —$SO_2R^{12}$,
  (e) hydroxy,
  (f) —O—$C_{1-6}$alkyl, which is unsubstituted or substituted with 1-5 halo,
  (g) —CN,
  (h) —$COR^{12}$,
  (i) —$NR^{10}OR^{11}$,
  (j) —$CONR^{10a}R^{11a}$,
  (k) —$CO_2R^9$,
  (l) —$(NR^{10a})CO_2R^9$,
  (m) —$O(CO)NR^{10a}R^{11a}$,
  (n) —$(NR^9)(CO)NR^{10a}R^{11a}$, and
  (o) oxo;
$R^9$ is independently selected from:
  (1) hydrogen,
  (2) —$C_{1-6}$alkyl, which is unsubstituted or substituted with 1-6 fluoro,
  (3) —$C_{3-6}$cycloalkyl,
  (4) benzyl, and
  (5) phenyl;
$R^{10}$ and $R^{11}$ are each independently selected from:
  (1) hydrogen,
  (2) $C_{1-6}$alkyl, which is unsubstituted or substituted with 1-6 fluoro,
  (3) —$C_{5-6}$cycloalkyl,
  (4) benzyl,
  (5) phenyl,
  (6) —$COR^9$, and
  (7) —$SO_2R^{12}$;
$R^{10a}$ and $R^{11a}$ are each independently selected from:
  (1) hydrogen,
  (2) —$C_{1-6}$alkyl, which is unsubstituted or substituted with 1-6 fluoro,
  (3) —$C_{5-6}$ cycloalkyl,
  (4) benzyl, and
  (5) phenyl;
or $R^{10a}$ and $R^{11a}$ join to form a ring selected from azetidinyl, pyrrolidinyl, piperidinyl, piperazinyl and morpholinyl, which ring is unsubstituted or substituted with 1-5 substituents each independently selected from: —$C_{1-6}$alkyl, —O—$C_{1-6}$alkyl, halo, hydroxyl, phenyl and benzyl;
$R^{12}$ is independently selected from:
  (1) —$C_{1-6}$alkyl, which is unsubstituted or substituted with 1-6 fluoro,
  (2) —$C_{5-6}$cycloalkyl,
  (3) benzyl, and
  (4) phenyl;
$R^{13}$ and $R^{14}$ are each independently selected from:
  (1) hydrogen,
  (2) —$C_{1-6}$alkyl, which is unsubstituted or substituted with 1-6 fluoro,
  (3) hydroxy, and
  (4) halo;
$R^{15}$ is selected from:
  (1) —$C_{1-6}$alkyl and —$C_{3-6}$cycloalkyl, which is unsubstituted or substituted with 1-7 substituents each independently selected from:
    (a) halo,
    (b) hydroxy,
    (c) —O—$C_{1-6}$alkyl,
    (d) —$C_{3-6}$cycloalkyl,
    (e) phenyl, which is unsubstituted or substituted with 1-5 substituents each independently selected from:
      (i) —$C_{1-6}$alkyl,
      (ii) —O—$C_{1-6}$alkyl,
      (iii) halo,
      (iv) hydroxy, and
      (v) trifluoromethyl, (f) —CO$_2$R$^9$, (g) —NR$^{10}$R$^{11}$, (h) —CONR$^{10}$OR$^{11}$, (i) —SO$_2$R$^{12}$, and (j) trifluoromethyl, and (2) phenyl or heterocycle, wherein said heterocycle is selected from: pyridyl, pyrimidinyl, pyrazinyl, thienyl and morpholinyl, which phenyl or heterocycle is unsubstituted or substituted with 1-5 substituents each independently selected from:

(a) —C$_{1-6}$alkyl, (b) —O—C$_{1-6}$alkyl, (c) halo, (d) hydroxy, and (e) trifluoromethyl;

m is 0 or 1;

n is 1 or 2;

p is 1 or 2;

or a pharmaceutically acceptable salt thereof, and individual enantiomers and diastereomers thereof.

2. The compound of claim 1, having the formula Ia:

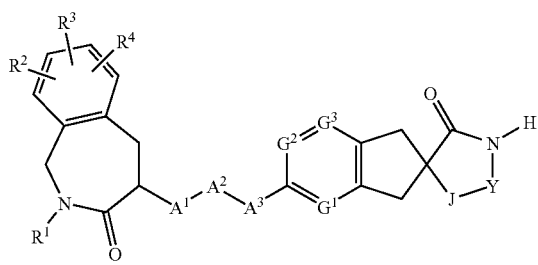

Ia or a pharmaceutically acceptable salt thereof, and individual enantiomers and diastereomers thereof.

3. The compound of claim 1, having the formula Ib:

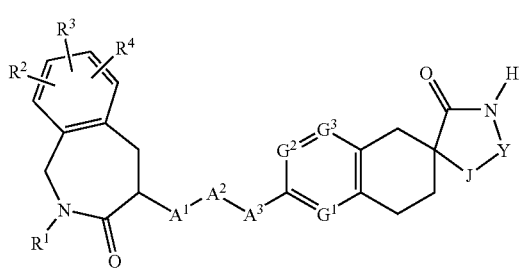

Ib or a pharmaceutically acceptable salt thereof, and individual enantiomers and diastereomers thereof.

4. The compound of claim 1, having the formula Ic:

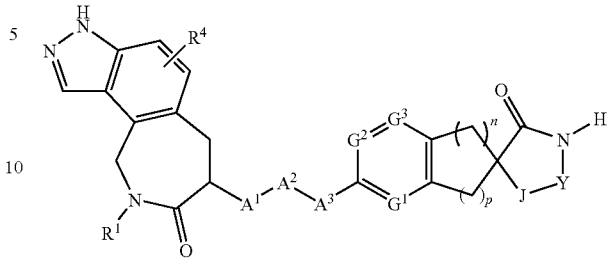

Ic or a pharmaceutically acceptable salt thereof, and individual enantiomers and diastereomers thereof.

5. The compound of claim 1, having the formula Id:

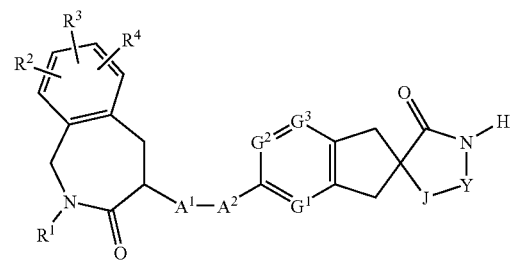

Id or a pharmaceutically acceptable salt thereof, and individual enantiomers and diastereomers thereof.

6. The compound of claim 1, having the formula Ie:

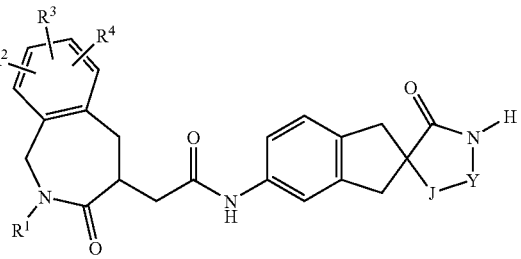

Ie or a pharmaceutically acceptable salt thereof, and individual enantiomers and diastereomers thereof.

7. The compound of claim 1, having the formula If:

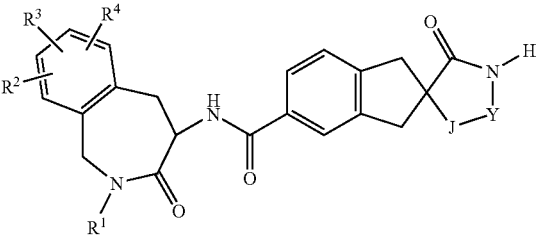

If or a pharmaceutically acceptable salt thereof, and individual enantiomers and diastereomers thereof.

8. A compound selected from:

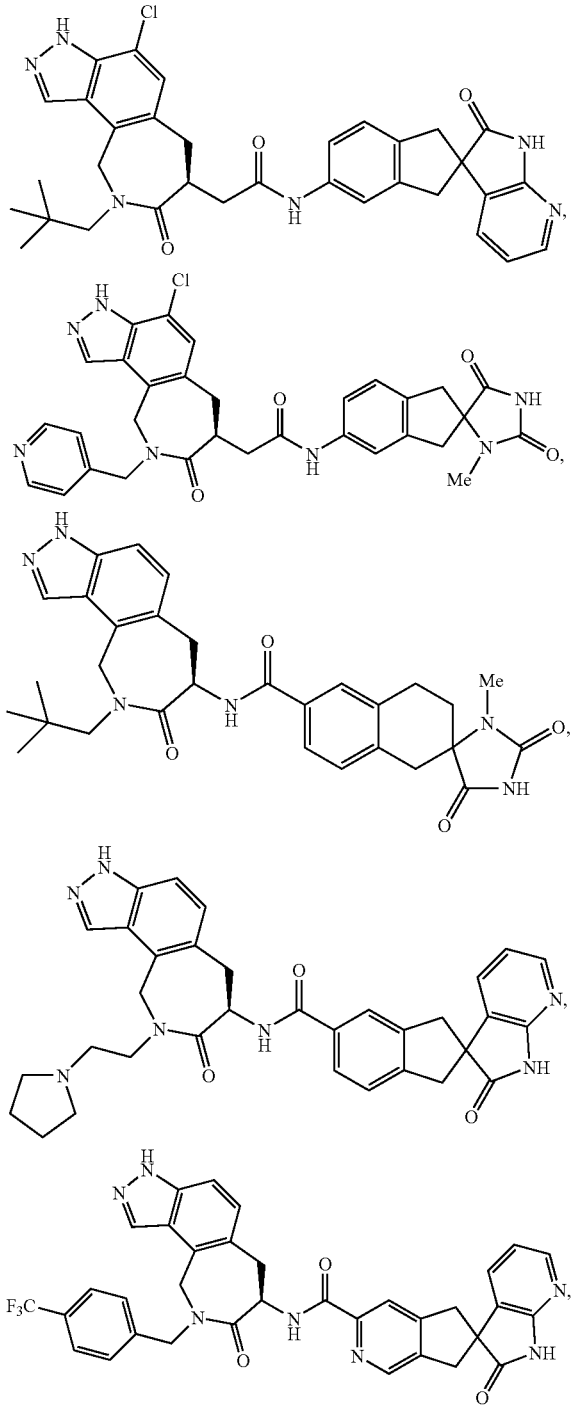

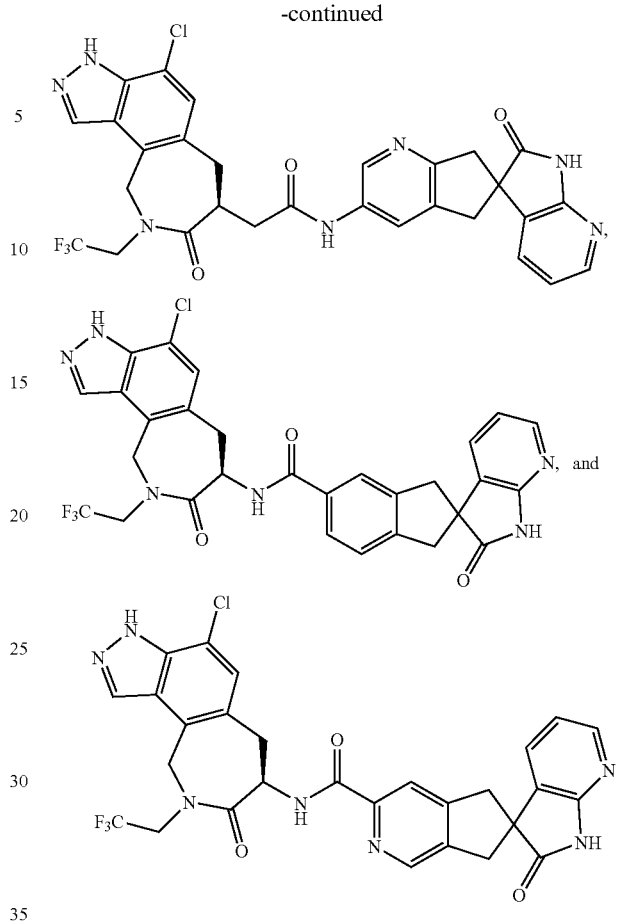

or a pharmaceutically acceptable salt thereof, and individual enantiomers and diastereomers thereof.

9. A pharmaceutical composition which comprises an inert carrier and the compound of claim 1.

10. A method for treating headache in a mammalian patient in need thereof, said method comprising the step of administering to said patient a therapeutically effective amount of the compound of claim 1.

11. A method for treating migraine headache or cluster headache in a mammalian patient in need thereof, said method comprising the step of administering to said patient a therapeutically effective amount of the compound of claim 1.

12. A method of treating migraine headaches or cluster headaches in a mammalian patient in need thereof, said method comprising the step of co-administration to said patient a therapeutically effective amount of the compound of claim 1 or a pharmaceutically acceptable salt thereof, and a therapeutically effective amount of a second agent selected from serotonin agonists, analgesics, anti-inflamatory agents, anti-hypertensives and anticonvulsants.

* * * * *